United States Patent [19]

Kouno et al.

[11] Patent Number: 5,360,926
[45] Date of Patent: Nov. 1, 1994

[54] PROCESS FOR PRODUCING METHYL METHACRYLATE

[75] Inventors: Seiji Kouno; Minoru Yasuda, both of Niihama, Japan

[73] Assignee: Sumitomo Chemical Company, Limited, Osaka, Japan

[21] Appl. No.: 139,754

[22] Filed: Oct. 22, 1993

[30] Foreign Application Priority Data

Oct. 22, 1992 [JP] Japan ................................ 4-284228
Feb. 18, 1993 [JP] Japan ................................ 5-028886

[51] Int. Cl.⁵ .............................................. C07C 69/52
[52] U.S. Cl. .................................................. 560/205
[58] Field of Search ........................................ 560/205

[56] References Cited

U.S. PATENT DOCUMENTS

| | | | |
|---|---|---|---|
| 3,579,309 | 5/1971 | Sennewald et al. | 23/288 |
| 3,924,290 | 10/1975 | Otsuki et al. | 260/486 R |
| 4,471,154 | 9/1984 | Franklin | 558/864 |

FOREIGN PATENT DOCUMENTS

| | | |
|---|---|---|
| 0273060 | 7/1988 | European Pat. Off. . |
| 2030324 | 11/1970 | France . |
| 1667139 | 6/1971 | Germany . |
| 73001369 | 2/1969 | Japan . |
| 61-004378 | 2/1986 | Japan . |

*Primary Examiner*—Paul J. Killos
*Attorney, Agent, or Firm*—Birch, Stewart, Kolasch & Birch

[57] ABSTRACT

An efficient process for producing methyl methacrylate which can give a high methacrylic acid conversion even when the mole ratio of methanol to methacrylic acid is small, said process comprises using an apparatus comprising a reaction zone having plural reaction sections connected in series and containing a strongly acidic ion-exchange resin and a distillation zone, feeding methacrylic acid to the first reaction section, feeding methanol to one or more reaction sections after the first reaction section, sending the reaction mixture formed in each reaction section to a reaction section just thereafter, feeding the vapor generated in each reaction section to a reaction section just therebefore, effecting simultaneously reaction and distillation in each reaction section of the reaction zone and distilling the vapor generated in the first reaction section in the distillation zone to separate methyl methacrylate.

9 Claims, 2 Drawing Sheets

5,360,926

PROCESS FOR PRODUCING METHYL METHACRYLATE

BACKGROUND OF THE INVENTION

This invention relates to a process for producing methyl methacrylate from methacrylic acid and methanol. More particularly, it relates to an improvement of a method for esterifying methacrylic acid with methanol using an ion-exchange resin.

Known methods for producing methyl methacrylate from methacrylic acid and methanol use sulfuric acid or a strongly acidic ion-exchange resin as a catalyst.

The method using a strongly acidic ion-exchange resin is lower in methacrylic acid conversion than the method using sulfuric acid; however, the former is collectively considered to be more advantageous than the latter because the former requires no process for treating sulfuric acid incorporated into an oil layer and low-grade materials may be satisfactorily used as the reactor materials.

The production of methyl methacrylate using a strongly acidic ion-exchange resin has heretofore been carried out in a fixed bed reactor. However, an equilibrium exists in the esterification reaction, and hence, when the reaction is effected in a fixed bed reactor, it is impossible to achieve the high conversion of methacrylic acid at the outlet of the reactor. In order to shift the equilibrium to the product side, usually the mole ratio of methanol to methacrylic acid is increased (see Japanese Patent Kokoku No. 61-4,378). In this case, unreacted methacrylic acid and unreacted methanol are separated from the reaction mixture and thereafter recycled to the reactor (see Japanese Patent Kokoku No. 48-1,369).

In the conventional method using a fixed bed reactor, the mole ratio of methanol to methacrylic acid is 1.2–2.0, and the method is carried out with a methacrylic acid conversion of 30–90%. Therefore, there is a problem that it follows that a large excess of methanol is recovered by distillation and hence the energy consumption is great. There is another problem that since the impurities contained in the starting material and polisher of methacrylic acid are deposited, the reaction mixture does not flow uniformly on the whole of the ion-exchange resin layer, the catalyst activity is degraded owing to contamination of the ion-exchange resin surface, and the catalyst life becomes extremely short.

In order to solve the above problems, it can be considered that the fixed bed reactor be replaced with a stirring type reactor or a fluidized bed reactor in which the ion-exchange resin is always in the fluid state. However, this cannot always achieve the high conversion of methacrylic acid unlike the method using the fixed bed reactor, and when it is intended to remove water and methyl methacrylate, which are products, by distillation while conducting the reaction, methanol is preferentially distilled out to water because the boiling point of the azeotropic mixture of methyl methacrylate and methanol is lower than that of water and not only is it impossible to shift the equilibrium to the product side but also dehydration operation becomes impossible because the distillate does not separate into two liquid layers.

SUMMARY OF THE INVENTION

Under such circumstances, the present inventors have made extensive research on a process for producing methyl methacrylate from methacrylic acid and methanol using a strongly acidic ion-exchange resin, and have, as a result, found that methyl methacrylate can be produced in good efficiency by continuously effecting reaction-distillation in multistage using an apparatus comprising a reaction zone having plural reaction sections connected in series and containing a strongly acidic ion-exchange resin and a distillation zone.

An object of this invention is to provide a process for producing methyl methacrylate from methacrylic acid and methanol using an apparatus comprising a reaction zone having plural reaction sections connected in series and containing a strongly acidic ion-exchange resin and a distillation zone.

Another object of this invention is to provide a process for producing methyl methacrylate in high efficiency with high methacrylic acid conversion.

Other objects and advantages of this invention will become apparent from the following description.

According to this invention, there is provided a process for producing methyl methacrylate from methacrylic acid and methanol which comprises feeding methacrylic acid and methanol to an apparatus comprising a reaction zone having plural reaction sections connected in series and containing a strongly acidic ion-exchange resin and a distillation zone, said methacrylic acid being fed to the first reaction section of the reaction zone, said methanol being fed to one or more reaction sections after the first reaction section, sending the reaction mixture formed in each reaction section to a reaction section just thereafter, sending the vapor generated in each reaction section to a reaction section just therebefore, continuously effecting reaction-distillation in each reaction section, distilling the vapor generated in the first reaction section of the reaction zone in the distillation zone to separate the methyl methacrylate produced.

BRIEF DESCRIPTION OF THE DRAWINGS

In FIG. 1, 101 refers to reaction-distillation column, 102 to reboiler, 103 to evaporator, 104 to condenser, 105 to separator, 106 to reaction zone, 107 and 108 to distillation zones, 109 to methacrylic acid-feeding line, 110 to methanol-feeding line, 111 to aqueous phase-withdrawing line, 112 to oil phase (ester phase)-withdrawing line, 113 to recycling line and 114 to high boiling matter-withdrawing line. In FIG. 2, 202a and 202b refer to reboilers, 204 to condenser, 205 to oil-water separator, 206a and 206b to reaction vessels, 206a' and 206b' to agitators, 207 to distillation zone, 209 to methacrylic acid-feeding line, 210 to methanol-feeding line, 211 to aqueous phase-withdrawing line, 212 to oil phase (ester phase)-withdrawing line, 215 to reaction mixture-withdrawing line, 216 to generated vapor-feeding line and 217 to reaction mixture-withdrawing line. In FIG. 3, 304 refers to condenser, 305 to oil-water separator, 306a–306d to reaction vessels, 306a'–306d' to agitators, 307 to distillation zone, 309 to methacrylic acid-feeding line, 310 to methanol-feeding line, 311 to aqueous phase-withdrawing line, 312 to oil phase (ester phase)-withdrawing line and 317 to reaction mixture-withdrawing line.

DETAILED DESCRIPTION OF THE INVENTION

Figure 2:
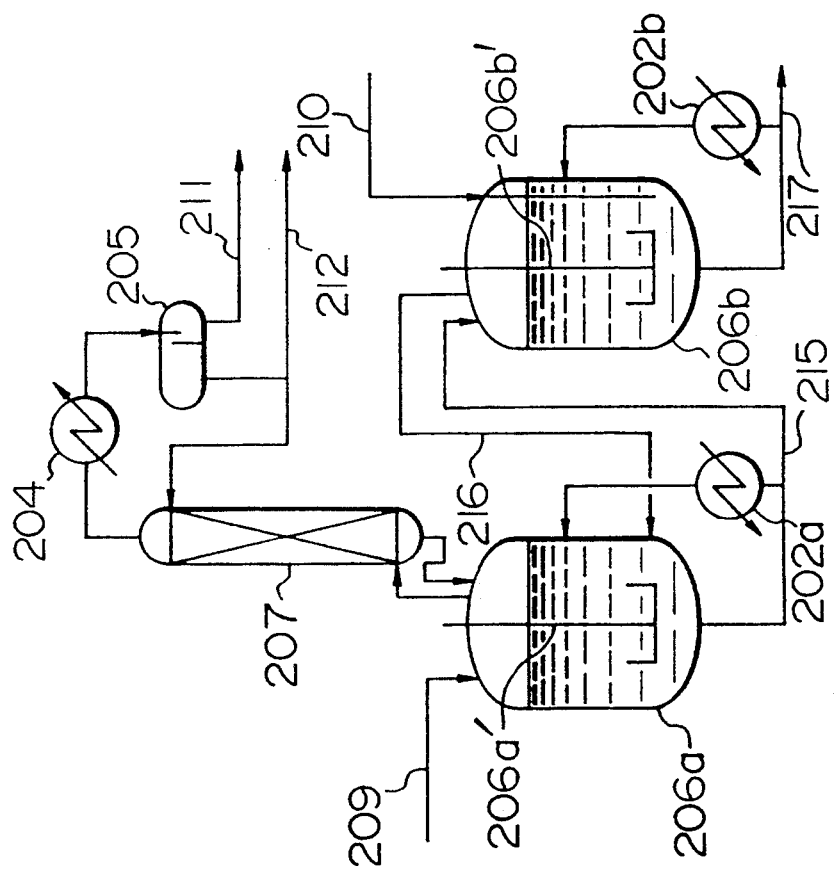
FIG. 2 is a view showing another embodiment of this invention and FIG. 3 is a view showing a further embodiment of this invention.

The strongly acidic ion-exchange resin used in this invention is not critical, and any commercially available strongly acidic ion-exchange resin may be used. In view of strength and reaction rate, Duolite (registered trade mark of Rohm & Haas) C-26C, Diaion (registered trade mark of Mitubish Kasei Kogyo K. K.) SK-1B, Nafion (registered trade mark of DuPont) NR-50 and the like are preferred.

The apparatus comprising a reaction zone having plural reaction sections connected in series and containing a strongly acidic ion-exchange resin and a distillation zone used in this invention may be a reaction-distillation column consisting essentially of a reaction zone composed of plural plates connected in series and containing a strongly acidic ion-exchange resin and a distillation zone, or an apparatus consisting essentially of a multistage successive reactor composed of 2 to 5 reaction vessels connected in series and containing a strongly acidic ion-exchange resin and a distillation column.

An explanation is made below of the case where the reaction-distillation column consisting of a reaction zone composed of plural plates connected in series and containing a strongly acidic ion-exchange resin and a distillation zone is used.

In this case, methyl methacrylate is produced by feeding methacrylic acid onto a plate on the upper side of the reaction zone, feeding methanol onto a plate in the lower side of the reaction zone, heating and evaporating a part of the bottom liquid in a feboiler connected to the reaction-distillation column, sending the vapor generated on each plate onto a plate just thereabove, sending the reaction mixture on each plate onto a plate just therebelow, fluidizing the ion-exchange resin on each plate with the vapor sent from the plate just therebelow, effecting simultaneously reaction and distillation on each plate, successively effecting the reaction and distillation in multistage, distilling the generated gas from the uppermost plate of the reaction zone in the distillation zone to distill out and separate methyl methacrylate from the top of the reaction-distillation column.

The reaction-distillation column used in this invention may be a conventional plate column, and when a sieve tray column or a ripple tray column is used, it is desirable to lay a net made of stainless steel, teflon or the like on the tray in order to prevent the strongly acidic ion-exchange resin from being passed through.

An embodiment of this invention is explained below referring to FIG. 1. The reaction-distillation column 101 has plural plates, and this plates portion is the reaction zone 106. Methacrylic acid is fed onto the uppermost plate of the reaction zone 106 through the line 109 and methanol is fed onto a plate on the lower side of the reaction zone 106 through the line 110. Methanol and/or methacrylic acid may be fed in the liquid form or a part or the whole thereof may be gaseous. A part of the bottom liquid is heated and vaporized in the feboiler 102 of the reaction-distillation column 101. Below the methanol-feeding position, the reaction zone 106 having plural plates in which a strongly acidic ion-exchange resin is present is provided.

On each plate in the reaction zone 106 in which a strongly acidic ion-exchange resin is present, a liquid mixture of the starting material and the product is allowed to flow down through a downcomer (not shown), while the strongly acidic ion-exchange resin thereon is fluidized with a mixed gas of the starting material and the product rising from a plate just therebelow whereby reaction and distillation take place simultaneously. The reaction and the distillation are successively carried out in multistage. The resulting methyl methacrylate and water are successively allowed to rise and are distilled out from the uppermost plate of the reaction zone 106.

In order to prevent methacrylic acid from being distilled out from the uppermost plate of the reaction zone 106, it is preferable to provide a distillation column 107 having a theoretical plate number of 3-10 above the uppermost plate of the reaction zone 106. Also, in order to prevent the low boiling matter such as methanol, water and the like sent to the bottom from being escaped, it is preferable to provide a distillation zone 108 having a theoretical plate number of 2-4 below the lowermost plate of the reaction zone 106. The residue of the bottom liquid is evaporated in the evaporator 103 and high boiling matter is taken out through the line 114 while the vaporizable component consisting mainly of methacrylic acid is recycled to the upper side of the reaction zone 106 through the line 113.

The gas distilled out from the distillation column 107 consisting mainly of methyl methacrylate and water which are the products is condensed in the condenser 104, and subjected to oil-water separation in the oil-water separator 105, and the water separated is then taken out through the line 111. A part of the oil phase (ester phase) separated is returned to the top of the distillation column 107 and the remainder of the oil phase is taken out as the product methyl methacrylate through the line 112. Usually, this is further purified by distillation or the like to be made a final product.

The larger the plate number of the reaction zone 6, the shorter the overall liquid residence time of the apparatus can be made; however, it cannot always be said that the larger the plate number the better. The plate number of more than about 20 is practically insignificant. This is because the concentration of either methanol or methacrylic acid in the liquid becomes sufficiently small and hence the reaction rate becomes approximately zero. Usually, a plate number of about 15-20 is used.

The methanol-feeding position is preferably a plate above the lowermost plate. When the reaction zone 106 has a plate number of 20, and if methacrylic acid is fed onto the first plate (the uppermost plate) of the reaction zone, methanol is preferably fed onto one of the 14th-17th plates. When methanol is fed onto a plate above these plates the methanol content on a plate near the lowermost plate becomes approximately zero and the plate does not work as a reaction plate. When methanol is fed onto a plate below the 14th-17th plates, the reaction rate becomes too small on a plate just above the feeding plate and the overall reacted amount is reduced. When the reaction zone 106 has a plate number of 5 or more, the optimum methanol-feeding plate is other than the lowermost plate. Methanol may be fed onto 2 or 3 plates of the reaction zone 106.

An explanation is made below of the case of use of an apparatus consisting of a multistage successive reactor having 2-5 reaction vessels and a distillation column.

In this case, methyl methacrylate is produced by feeding methacrylic acid to the first reaction vessel and methanol to one or some of the 2nd–5th reaction vessels, sending the reaction mixture in each reaction vessel to a reaction vessel just thereafter, sending the vapor generated in each vessel to a reaction vessel just therebefore, effecting reaction and distillation in each reaction vessel, feeding simultaneously therewith the vapor generated in the first reaction vessel to the distillation column while circulating the bottom liquid of the distillation column to the first reaction vessel and separating methyl methacrylate from the top of the distillation column.

The distillation column used in this invention may be any conventional distillation column such as packed column, perforated plate column, plate column or the like and the column type is not critical. The reaction vessel may be any vessel having a means capable of fluidizing the strongly acidic ion-exchange resin, for example, a stirring type reaction vessel, a fluidizing type reaction vessel or the like, and the vessel type and form are not critical. In the stirring type reaction vessel, there is preferably used an agitating blade having smooth edge such as a glass-lined anchor blade, a Pfaudler blade or the like in order to minimize the crushing of strongly acidic ion-exchange resin. The fluidizing type reaction vessel is of the type that the ion-exchange resin is fluidized with a rising stream caused by an inert gas such as nitrogen, air or the like; methanol vapor; a pump-circulating stream; or the like, and the type and form are not critical.

Another embodiment of this invention is explained below referring to FIG. 2. The apparatus of FIG. 2 is composed of two reaction vessels 206a and 206b and a distillation column 207, and the reaction vessels 206a and 206b have agitators 206a' and 206b', respectively. The distillation column 207 is connected to the reaction vessel 206a and methacrylic acid is fed to the reaction vessel 206a through the line 209 and methanol is fed to the reaction vessel 206b through the line 210. Methanol and/or methacrylic acid is fed in the liquid form or a part or the whole thereof may be gaseous. The reaction vessels 206a and 206b have exterior heaters or jackets 202a and 202b, respectively (in FIG. 2, exterior heaters are shown), which heat the reaction mixtures to the respective desired temperatures to boil and evaporate them. In each of the reaction vessels, there is a three-phase system of gas-liquid-solid including the strongly acidic ion-exchange resin, which system is kept in a mixed fluid state by applying the desired electric power thereto.

Only the reaction mixture is taken out from the bottom of the reaction vessel 206a through a filter (not shown), and sent to the reaction vessel 206b through the line 215. In this case, the feeding position may be in the gaseous phase portion or in the liquid phase portion. On the other hand, the vapor generated in the reaction vessel 206b is fed in the gaseous form through the line 216 into the liquid in the reaction vessel 206a. The above two transfers are effected simultaneously so that gas-liquid countercurrent contact can be conducted between the two vessels. The desired withdrawal of the liquid from the bottom of the reaction vessel 206b is effected via the line 217 through a filter (not shown). The withdrawn liquid comprises mainly the starting methacrylic acid and the product methyl methacrylate and also contains a slight amount of high boiling by-products, so that the high boiling fraction is cut and the residue thereof is then recycled to the reaction vessel 206a (recycling is not shown).

From the reaction vessel 206a, methyl methacrylate and water are fed in the gaseous form to the distillation column 207. In order to prevent methacrylic acid from being escaped from the top of the distillation column 207, it is preferable that the distillation column 207 is designed to have a theoretical plate number of about 3–10, and operated at a reflux ratio of 1.0 or more. The distillate gas from the top of the distillation column 207 which comprises mainly methyl methacrylate and water which are the products is condensed in the condenser 204 and subjected to oil-water separation in the oil-water separator 205. The aqueous phase separated is taken out from the line 211. A part of the oil phase (ester phase) is returned to the top of the distillation column 207 and the residue of the oil phase is taken out as a product methyl methacrylate from the line 212. Usually, this product is further purified by distillation to be made final product.

The larger the number of the reaction vessels, the shorter the overall liquid residence time in the reactor can be made; however, it cannot always be said that the larger the number of the reaction vessels the better. More than 20 reaction vessels are practically insignificant because the concentration of either the starting methanol or the starting methacrylic acid in the liquid becomes too low in some of the reaction vessels whereby the reaction rate becomes approximately zero. In fact, taking the equipment cost into consideration, usually, the reaction is conducted in 2–5 reaction vessels.

Figure 3:
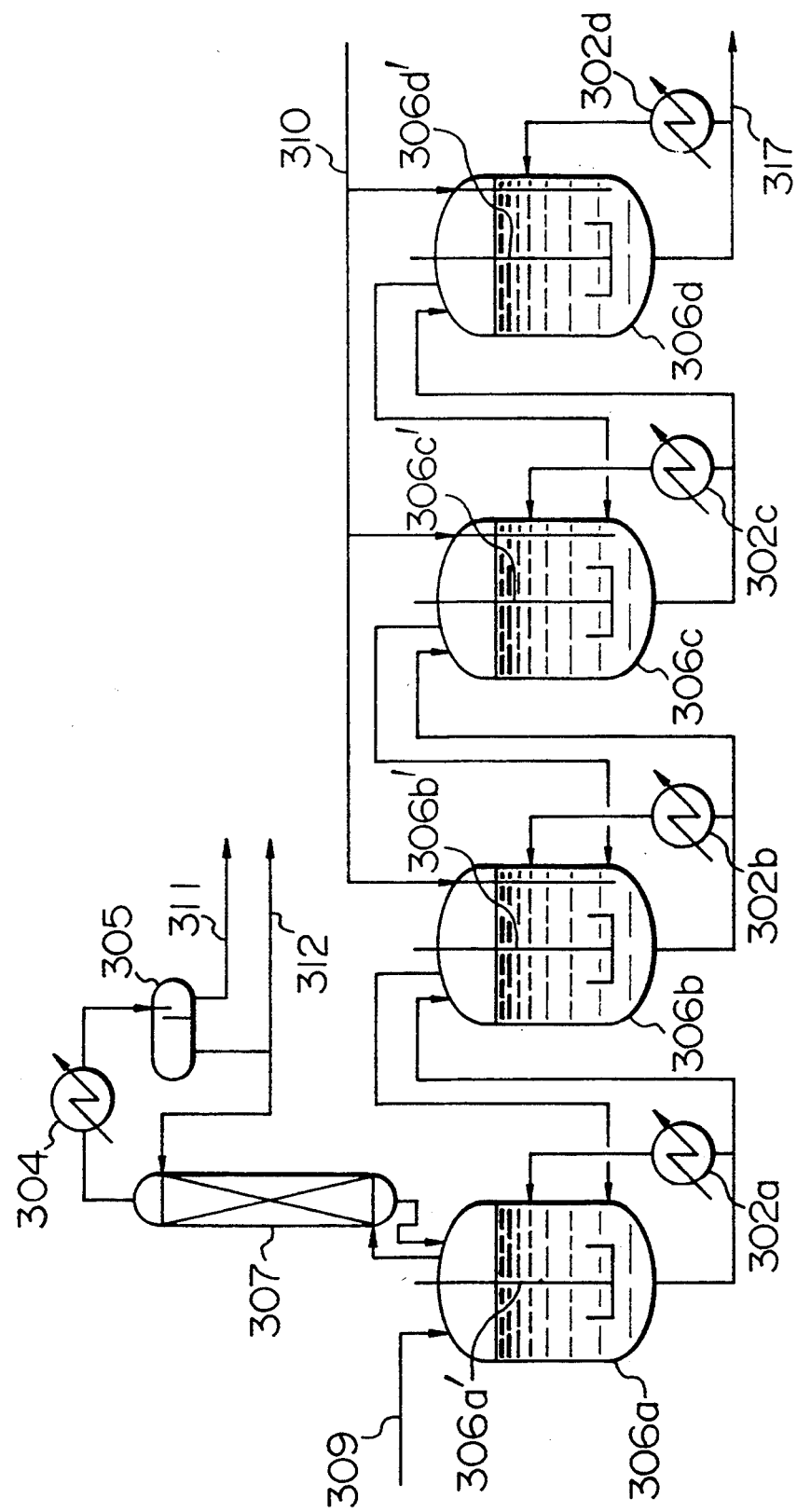

FIG. 3 shows an example of an apparatus comprising 4 reaction vessels and a distillation column.

When the reaction is effected in 3 or more reaction vessels, the starting methanol is fed to one or more reaction vessels after the first reaction vessel to which the starting methacrylic acid is fed. When methanol is fed to one reaction vessel, it is not always good to feed it to the final reaction vessel. For example, in the case of 5 reaction vessels, the methanol-feeding position is most preferably the 4th reaction vessel. This is because the overall reaction rate of the whole system is varied depending upon the methanol-feeding position and it is the highest when methanol is fed to the 4th reaction vessel. Methanol must not be fed to the reaction vessel 306a connected to the distillation column 307 because the liquid phase in the reaction vessel 306a comes to have a composition rich in methanol and the vapor generated in the reaction vessel 306a becomes a methanol-methyl methacrylic acid azeotropic mixture having the lowest boiling point, whereby it becomes impossible to take out effectively water from the system. Accordingly, as a matter of course, when the reaction is effected in one reaction vessel, dehydration cannot be conducted. Also, the liquid withdrawn from the final reaction vessel 306d is, if necessary, subjected to removal of high boiling matters, and thereafter, recycled to any one of the reaction vessels before the final reaction vessel. Usually, the withdrawn liquid is recycled to the first reaction vessel to which methacrylic acid is fed though this is not critical.

The operation of this reaction apparatus is not critical; however, the reaction apparatus is usually operated by feeding the predetermined amounts of methacrylic acid and methanol, setting the pressure of the distillation column, applying heat in the amount necessary for effecting the desired boiling to the reaction vessels while conducting the necessary control, and controlling the amount of the liquid withdrawn from each reaction vessel so that the liquid level in each reaction vessel becomes constant. The amount of methacrylic acid and methanol fed are suitably increased or decreased observing the distillate amount and the liquid level control state.

In the process of this invention, the reaction pressure and the reaction temperature are not critical; however, it is preferable to conduct the operation at a pressure of about 500 Torr to atmospheric pressure at the top of distillation column at a temperature of about 70°–90° C. in the distillation column at a temperature of about 80°–120° C. in the reaction zone.

Even when the process of this invention is carried out at a low mole ratio of methanol to methacrylic acid of 1.01–1.20, the conversion of methacrylic acid is increased to 90–99.9% and methyl methacrylate can efficiently be produced.

DESCRIPTION OF PREFERRED EMBODIMENTS

This invention is further explained in more detail below referring to Examples, which are not by way of limitation but by way of illustration.

Example 1

Figure 1:
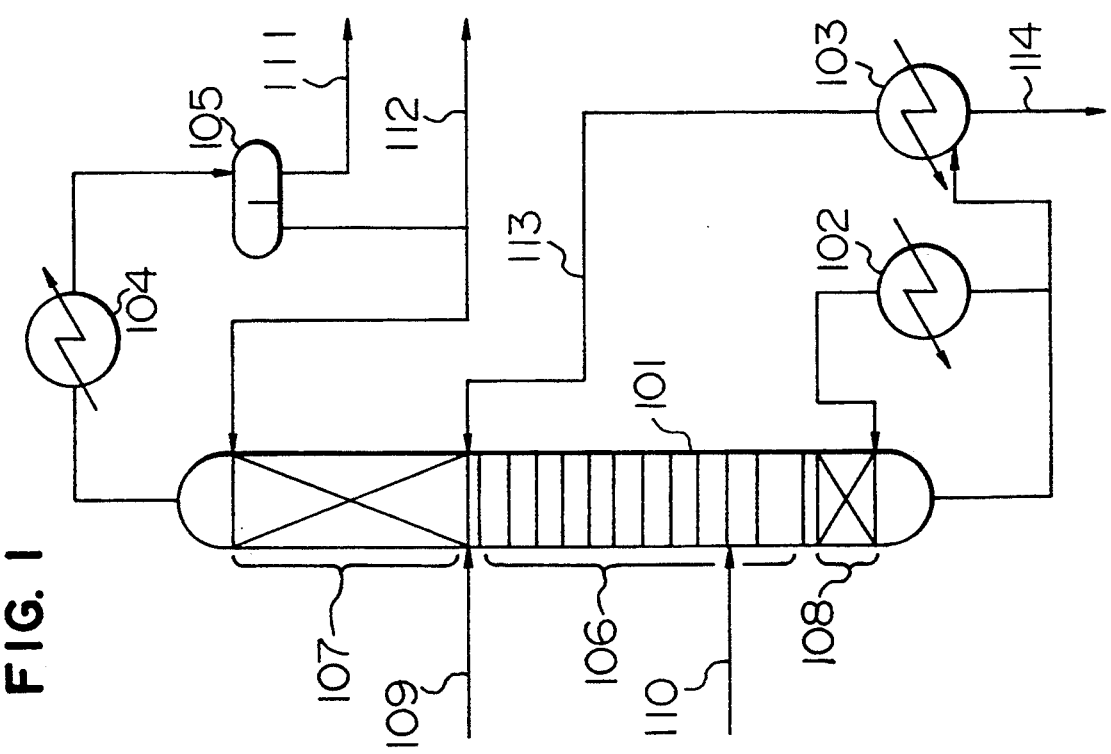
FIG. 1 is a view showing an embodiment of this invention.

Methyl methacrylate was produced from methacrylic acid and methanol using the same multistage reaction-distillation column as shown in FIG. 1. The reaction-distillation column had an inner diameter of 0.1 m, and was composed of a reaction zone having a theoretical plate number of 20, a distillation zone having a theoretical plate number of 5 above the reaction zone and a distillation zone having a theoretical plate number of 2 below the reaction zone. Each plate of the reaction zone was packed with 0.1 liter of Duolite (trade mark of Rohm & Haas) C-26C which is a strongly acidic ion-exchange resin. Methacrylic acid was fed in the liquid form at a rate of 1.0 kg/hr onto the 6th plate from the top plate of the column (the 1st plate of the reaction zone). Methanol was fed in the liquid form at a rate of 0.41 kg/hr to the 19th plate (the 14th plate of the reaction zone) (the mole ratio of methanol to methacrylic acid is 1.1). Reaction-distillation was conducted at a top pressure of 500 Torr at a top temperature of 74° C. at a bottom pressure of 600 Torr and at a bottom temperature of 86° C. Incidentally, a half of the bottom liquid was evaporated and returned to the bottom to heat the reaction-distillation column. The residue of the bottom liquid was subjected to removal of high boiling matter and then returned in the gas phase onto the 1st plate of the reaction zone. In the column, the 19th plate was at the lowest temperature of 73° C. and the 6th plate was at the highest temperature of 114° C. Incidentally, the liquid residence time in the reaction zone was 0.43 hour.

The vapor boiled in the reboiler rose in the column to fluidize the strongly acidic ion-exchange resin. The vapor from the column top was condensed to find that the composition thereof was water 8.9% by weight, methanol 2.3% by weight, methyl methacrylate 88.3% by weight and methacrylic acid 0.35% by weight. The distillate was separated into an oil phase (ester phase) and an aqueous phase. The aqueous phase was taken out at a rate of 0.21 kg/hr and a half of the oil phase was returned to the top of the distillation column and the residue of the oil phase was taken out as a product at a rate of 1.14 kg/hr.

The composition of the ester phase was water 2.0% by weight, methanol 1.9% by weight, methyl methacrylate 95.7% by weight and methacrylic acid 0.36% by weight.

The substantially remaining methacrylic acid was only the methacrylic acid contained in the ester phase taken out from the column top, and the methacrylic acid conversion in said reaction-distillation was 99.6%.

Example 2

Methyl methacrylate was produced from methanol and methacrylic acid using the same apparatus consisting of two reaction vessels and one distillation column as shown in FIG. 2, provided that the liquid in the reaction vessel was heated by the jacket. As the reaction vessels, two 2.2-liter glass separable flasks were used. To the 1st reaction vessel 206a were fed 7.1 g of methanol, 14 g of water, 500 g of methyl methacrylate, 480 g of methacrylic acid and 400 g of an ion-exchange resin [(Duolite (a registered trade mark of Rohm & Haas) C-26C, density: 400 dry g/liter], and to the second reaction vessel 206b were fed 11 g of methanol, 11 g of water, 374 g of methyl methacrylate, 604 g of methacrylic acid and 400 g of the same ion-exchange resin as above. The distillation column 207 was a packed column having a theoretical plate number of 5 consisting of a glass column having an inner diameter of 30 mm filled with a dixson packing.

The reaction vessels were stirred with a glass anchor blade at the necessary electric power of 0.25 kw/m$^3$. Methacrylic acid was fed in the liquid form to the reaction vessel 206a connected to the distillation column 207 at a rate of 283.8 g/hr and methanol was fed in the liquid form to the reaction vessel 206b at a rate of 116.2 g/hr (the mole ratio of methanol to methacrylic acid was 1.1), to effect esterification reaction.

The pressure at the top of the distillation column 207 was adjusted to 650 Torr and the reaction was continued. After 50 hours, the temperature at the top of the distillation column was 80° C., the liquid temperature of the reaction vessel 206a was 95.6° C., and the liquid temperature of the reaction vessel 206b was 102.8° C. At this time, the amount of the contents withdrawn from the reaction vessel 206b was 57.0 g/hr (the residence time was 5.03 hours), the aqueous phase was withdrawn at a rate of 59.6 g/hour from the oilwater separator, a half of the oil phase was returned to the upper side of the distillation column 207, and the residue of the oil phase was obtained as a product at a rate of 308.4 g/hr.

The composition of the condensate obtained by condensing the distillate gas from the top of the column was 9.2% by weight of water, 4.1% by weight of methanol, 86.7% by weight of methyl methacrylate and 340 ppm of methacrylic acid. The composition of the oil phase was 2.3% by weight of water, 3.3% by weight of methanol, 94.4% by weight of methyl methacrylate and 350 ppm of methacrylic acid. The methacrylic acid conversion was 93.2%.

What is claimed is:

1. A process for producing methyl methacrylate from methacrylic acid and methanol, which comprises feeding methacrylic acid and methanol to an apparatus comprising a reaction zone having plural reaction sections connected in series and containing a strongly acidic ion-exchange resin and a distillation zone, said methacrylic acid being fed to the first reaction section of the reaction zone and said methanol being fed to one or more reaction sections after the first reaction section, sending the reaction mixture formed in each reaction section to a reaction section just thereafter, sending the vapor generated in each reaction section to a reaction section just therebefore, effecting simultaneously reaction and distillation in each reaction section, and distilling the vapor generated in the first reaction section of the reaction zone in the distillation zone to separate the methyl methacrylate produced.

2. The process for producing methyl methacrylate according to claim 1, wherein the apparatus comprising a reaction zone having plural reaction sections connected in series and containing a strongly acidic ion-exchange resin and a distillation zone is a reaction-distillation column consisting essentially of a reaction zone composed of plural plates connected in series and containing a strongly acidic ion-exchange resin and a distillation zone or an apparatus consisting essentially of a multistage successive reactor composed of 2 to 5 reaction vessels connected in series containing a strongly acidic ion-exchange resin and a distillation column.

3. The process for producing methyl methacrylate according to claim 1, wherein the apparatus comprising a reaction zone and a distillation zone is a reaction-distillation column consisting essentially of a reaction zone composed of plural plates connected in series and containing a strongly acidic ion-exchange resin, methacrylic acid is fed onto a plate on the upper side of the reaction zone, methanol is fed onto a plate on the lower side of the reaction zone, a part of the bottom liquid is heated and evaporated in a reboiler connected to the reaction-distillation column, the vapor generated on each plate is sent onto a plate just thereabove, the reaction mixture formed on each plate is sent onto a plate just therebelow, the ion-exchange resin is fluidized on each plate with the vapor rising from the plate just therebelow, reaction and distillation are, simultaneously therewith, effected in multistage, the vapor generated in the uppermost plate of the reaction zone is distilled in the distillation zone, to distill out and separate methyl methacrylate from the top of the reaction-distillation column.

4. The process for producing methyl methacrylate according to claim 3, wherein the plate number of the reaction zone composed of plural plates connected in series and containing a strongly acidic ion-exchange resin of the reaction-distillation column is 15–20.

5. The process for producing methyl methacrylate according to claim 3, wherein a distillation zone is provided on the upper side and/or the lower side of the reaction zone.

6. The process for producing methyl methacrylate according to claim 3 or 5, wherein the reaction zone is provided below the methanol-feeding plate.

7. The process for producing methyl methacrylate according to claim 1, wherein the apparatus comprising a reaction zone and a distillation zone is an apparatus consisting essentially of a multistage successive reactor having 2 to 5 reaction vessels in which the strongly acidic ion-exchange resin is fluidized, and a distillation column, methacrylic acid is fed to the first reaction vessel, methanol is fed to 1–4 reaction vessels after the first reaction vessel, the reaction mixture in each reaction vessel is sent to a reaction vessel just thereafter, the vapor generated in each reaction vessel is sent to a reaction vessel just therebefore, reaction and distillation are simultaneously effected in each reaction vessel, the vapor generated in the first reaction vessel is, simultaneously therewith, fed to the distillation column, the bottom liquid of the distillation column is circulated to the first reaction vessel and methyl methacrylate is separated from the top of the distillation column.

8. The process for producing methyl methacrylate according to claim 1, 2 or 7, wherein the reaction vessel is a stirring type reaction vessel or a fluidizing type reaction vessel.

9. The process for producing methyl methacrylate according to claim 1, 3 or 7, wherein the mole ratio of methanol to methacrylic acid is 1.01–1.20.

* * * * *